US00PP23285P3

(12) United States Plant Patent
Pavlich

(10) Patent No.: US PP23,285 P3
(45) Date of Patent: Dec. 25, 2012

(54) ***HEUCHERA* PLANT NAMED 'BERRY MARMALADE'**

(50) Latin Name: ***Heuchera* spp.**
Varietal Denomination: Berry Marmalade

(76) Inventor: John C. Pavlich, Olympia, WA (US)

( * ) Notice: Subject to any disclaimer, the term of this patent is extended or adjusted under 35 U.S.C. 154(b) by 127 days.

(21) Appl. No.: 13/066,131

(22) Filed: Apr. 6, 2011

(65) Prior Publication Data

US 2012/0260382 P1 Oct. 11, 2012

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu

(74) *Attorney, Agent, or Firm* — Klarquist Sparkman, LLP

(57) ABSTRACT

A new and distinct *Heuchera* plant substantially as shown and described, characterized by deep purple black spring leaves, glossy purple black summer leaves, ruffled leaves, medium large plant size, and excellent vigor.

1 Drawing Sheet

Botanical denomination: *Heuchera* spp.
Variety designation: 'Berry Marmalade'.

BACKGROUND OF THE INVENTION

The present invention relates to a new and distinct cultivar of *Heuchera* and given the cultivar name of 'Berry Marmalade'. *Heuchera* is in the family Saxifragaceae. *Heuchera* 'Berry Marmalade' originated from a planned cross in Olympia, Wash. between *Heuchera* 'Obsidian' (U.S. Plant Pat. No. 14,836), as the seed parent, and *Heuchera* 'Sparkling Burgundy' (U.S. Plant Pat. No. 17,208), as the pollen parent.

Compared to the seed parent, *Heuchera* 'Obsidian', the new cultivar has a larger habit and leaves that are undulate and dark purple rather than black.

Compared to the pollen parent, *Heuchera* 'Sparkling Burgundy', the new cultivar has leaves that are darker and flowers that are brown rather than white.

Compared to *Heuchera* 'Amethyst Mist' (an unpatented plant), the new cultivar has a tighter habit, shorter flowers, more ruffled leaves, and darker purple foliage that holds its dark color all summer.

This new *Heuchera* is distinguished by:

1. deep purple black spring leaf color,
2. glossy purple black summer leaves,
3. medium large plant size,
4. ruffled leaves,
5. and excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two-year-old *Heuchera* 'Berry Marmalade' in bloom, growing in the trail field in early June in Canby, Oreg.

DETAILED PLANT DESCRIPTION

The following is a detailed description of the new *Heuchera* cultivar based on observations of two-year-old specimens grown in the garden in full sun in April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Basal rosette, herbaceous perennial.
*Hardiness*.—USDA Zone 4 to 9.
*Size*.—25 cm tall from top of the foliage to the ground and 46 cm wide.
*Habit*.—Mounding.
*Vigor*.—Excellent.
*Roots*.—Fibrous, freely branching, fine, and white in color; roots develop easily from cuttings.

Leaf:

*Type*.—Simple.
*Arrangement*.—Basal.
*Shape*.—Ovate to orbicular.
*Lobing/division*.—5 main lobes, with 2 to 3 secondary lobes.
*Venation*.—Palmate.
*Margins*.—Crenate and undulate.
*Apex*.—Mucronulate.
*Base*.—Cordate.
*Blade size*.—Grows to 10 cm long and 10 cm wide.
*Surface texture*.—Both sides glandular.
*Petiole description*.—Grows to 16 cm long and 3 mm wide, glandular hairs, Greyed Purple N186C.
*Leaf color*.—Spring and fall, top side, Purple N77A with veins Greyed Purple N186A, bottom side N79A; summer topside Greyed Purple N187A bottomside Greyed Purple N186A.

Inflorescence:

*Size*.—Grows to 6.5 cm wide and 30 cm long.

*Type*.—Thyrse.

*Number of flowers per thyrse*.—About 120 per thyrse.

*Number of thyrse*.—About 24 in first spring bloom.

*Peduncle*.—Grows to 21 cm tall and 7 mm wide at base, Greyed Purple N187A, glandular hairs, with 5 or more petiolate leaves (ovate, blades grow to 6.5 cm long and 6 cm wide, 5 lobed with the terminal lobe the longest, margin crenate, Purple N77A on top side, bottom side N186C).

*Pedicel*.—Variable in size, with glandular hairs, Greyed Purple N187A.

*Bloom period*.—Late May to June in Canby, Oreg.

Flower bud:

*Size*.—2.5 mm wide and 5 mm long.

*Description*.—Glandular puberulent, ovoid.

*Color*.—Top ⅓ Yellow Green 152D to bottom ⅔ Greyed Purple 187B.

Flower:

*Type*.—Perfect.

*Shape*.—Campanulate.

*Size*.—5 mm long and 4 mm wide.

*Petal description*.—5 in number, 3 mm long, linear to spatulate with a clawed base, reflexed, tip acute, margin entire, glabrous on top, sparsely glandular on bottom side, White NN155B on both sides.

*Calyx description*.—4 mm long and 3 mm wide, with 5 lobes, divided ½ way to the base, glandular hairs on outside, glabrous inside, tip obtuse, margin entire, both sides Yellow Green 153A tinted Greyed Purple 187B.

*Stamen description*.—5 in number, 2 mm long, filaments Green White 157D, anthers Greyed Yellow 161A, no pollen, male sterile.

*Pistil description*.—One central two beaked pistil, 4 mm long, ovary 2 mm long and Yellow Green 144C, style 2 mm long, Yellow Green 144D.

*Fragrance*.—None.

*Lastingness*.—Each thyrse blooms for about 2 weeks on the plant.

Fruit:

*Type*.—Two beaked capsule.

*Size*.—5 mm deep by 2 mm wide.

*Fertility*.—Good.

*Color*.—Greyed Brown 199A.

Seed:

*Shape*.—Linear.

*Size*.—2 mm long.

*Color*.—Black, RHS 202A.

Disease and pest tolerance: No known resistances. Excellent disease tolerance to powdery mildew and *Heuchera* rust. All *Heuchera* are susceptible to root weevils.

I claim:

1. A new and distinct *Heuchera* plant as herein illustrated and described.

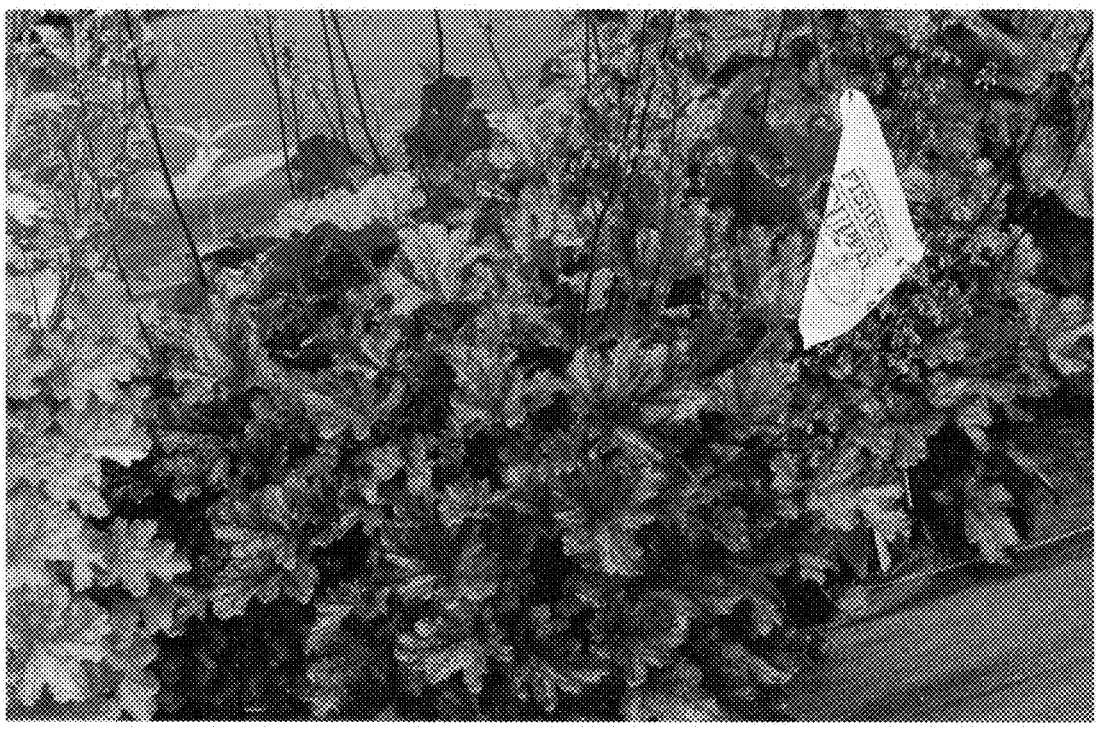

* * * * *